United States Patent [19]

Wonderley et al.

[11] Patent Number: 5,309,641
[45] Date of Patent: May 10, 1994

[54] DISPOSABLE SURGICAL SCALPEL WITH SAFETY GUARD

[75] Inventors: Jeff W. Wonderley, Ft. Defiance; Donald G. Strickland, Charlottesville, both of Va.

[73] Assignee: American Safety Razor Company, Verona, Va.

[21] Appl. No.: 986,741

[22] Filed: Dec. 8, 1992

Related U.S. Application Data

[63] Continuation-in-part of Ser. No. 808,891, Dec. 18, 1991.

[51] Int. Cl.⁵ .................. B26B 3/02; B26B 1/04; B26B 1/10
[52] U.S. Cl. ........................ 30/339; 30/151; 606/167
[58] Field of Search ............... 30/320, 329, 332, 333, 30/334, 335, 339, 151, 156, 157, 160, 162; 606/167, 172, 181

[56] References Cited

U.S. PATENT DOCUMENTS

| | | | |
|---|---|---|---|
| 2,304,332 | 12/1942 | Bodkin | 30/335 |
| 3,412,467 | 11/1968 | Matwijcow | 30/335 |
| 3,889,368 | 6/1975 | Himeno | 30/162 |
| 3,905,101 | 9/1975 | Shepherd | 30/162 |
| 3,906,626 | 9/1975 | Riuli | 30/162 |
| 4,523,379 | 6/1985 | Osterhout et al. | 30/151 |
| 4,576,164 | 3/1986 | Richeson | 128/305 |
| 4,719,915 | 1/1988 | Porat et al. | 128/305 |
| 4,735,202 | 4/1988 | Williams | 128/305 |
| 4,768,509 | 9/1988 | Grosvenor et al. | 128/305 |
| 4,803,751 | 2/1989 | Cousins | 15/236 |
| 4,958,625 | 9/1990 | Bates et al. | 128/754 |
| 4,985,034 | 1/1991 | Lipton | 606/167 |
| 5,071,426 | 12/1991 | Dolgin et al. | 606/167 |
| 5,139,507 | 8/1992 | Dolgin et al. | 30/151 |

Primary Examiner—Richard K. Seidel
Assistant Examiner—Paul M. Heyrana, Sr.
Attorney, Agent, or Firm—Willian Brinks Olds Hofer Gilson & Lione

[57] ABSTRACT

A scalpel including an elongated handle having an engaging surface located on the handle, a blade carried by the handle adjacent one end thereof and a guard movably mounted to the handle for sliding movement relative to the handle between a protective position covering the blade and a retracted position exposing the blade for use. The guard includes side members extending downwardly from an upper surface. The side members are positioned adjacent opposite sides of the handle and the resiliency of the guard forces the inner surfaces of the side members into engagement with the engaging surface of the handle. The guard is movably along the engaging surface in response to sliding movement of the guard relative to the handle. In a further form, the guard is slidable into a permanently locked position relative to the handle, thereby preventing reuse of the scalpel and inadvertent exposure of the blade.

18 Claims, 13 Drawing Sheets

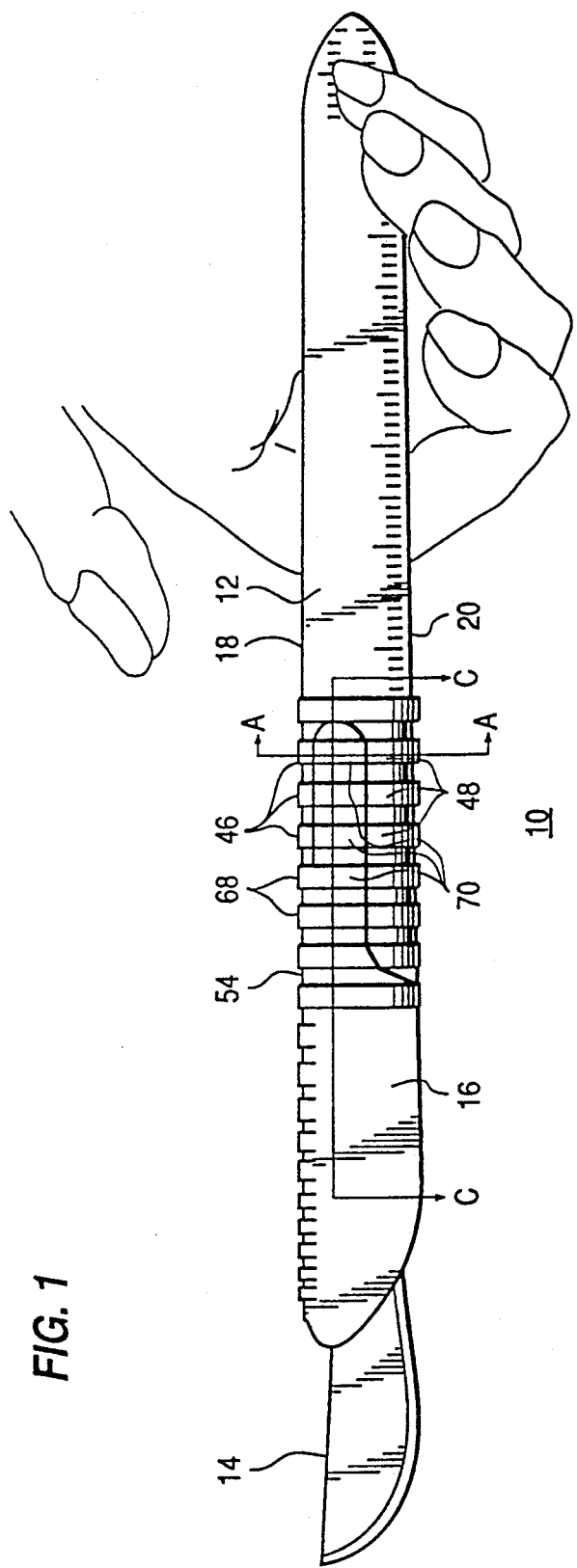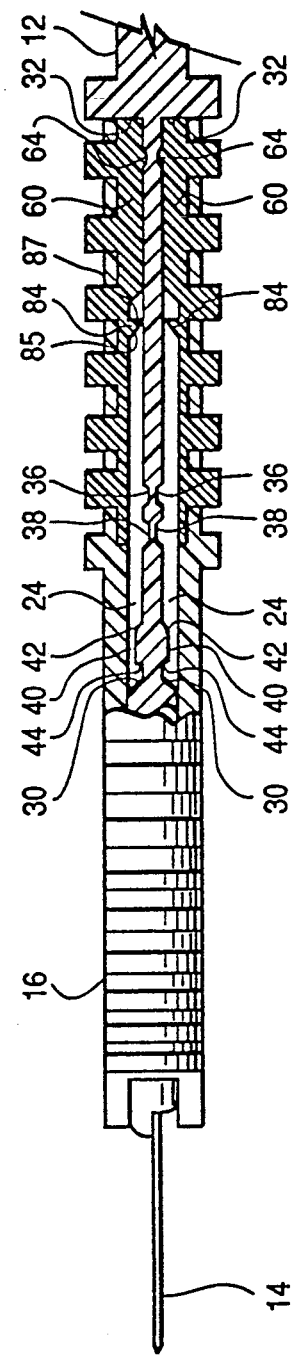

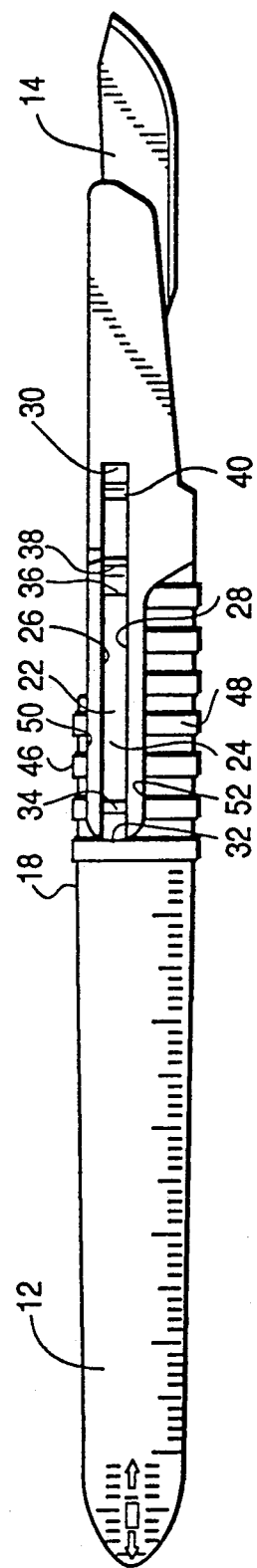

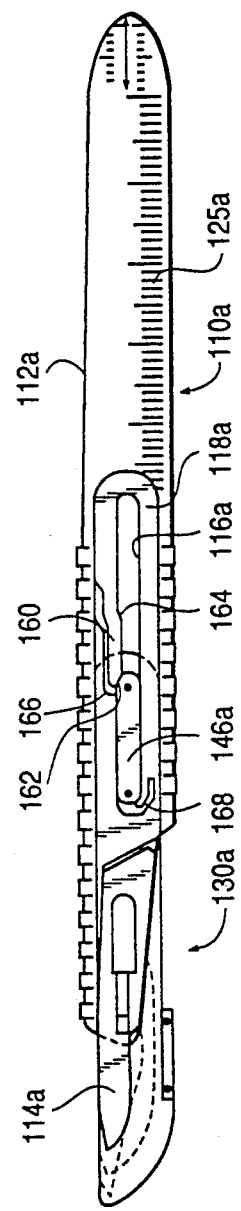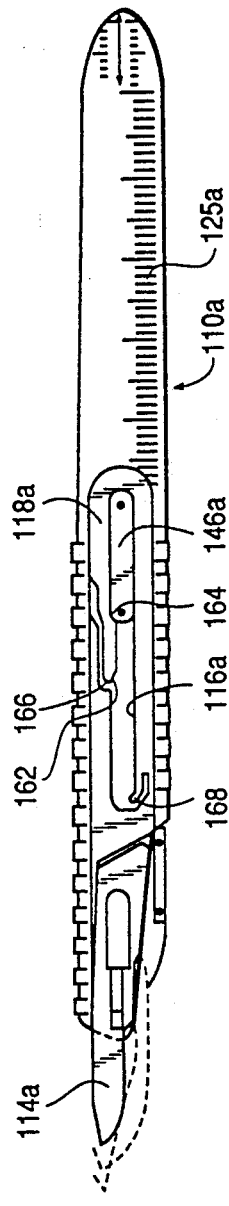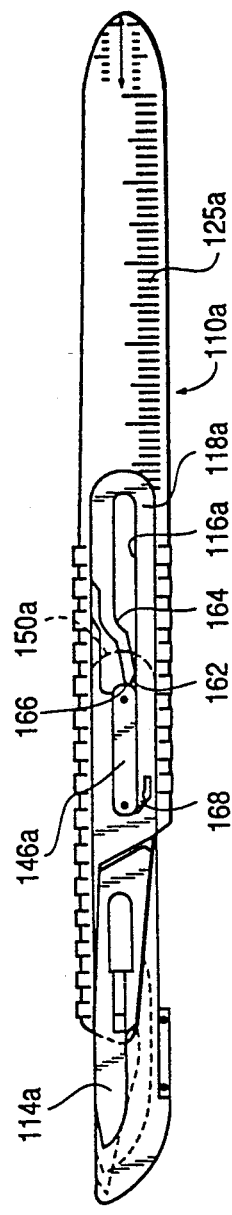

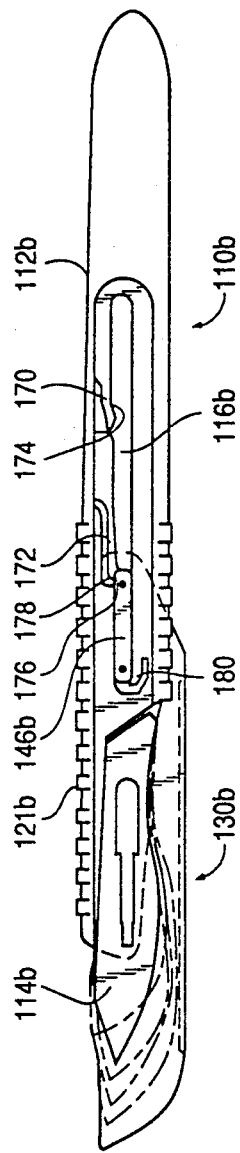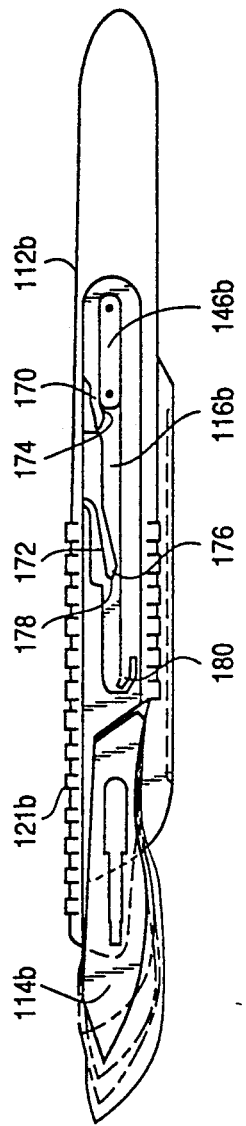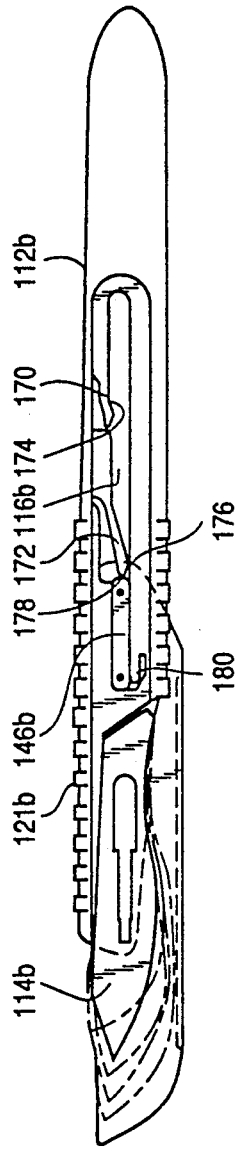

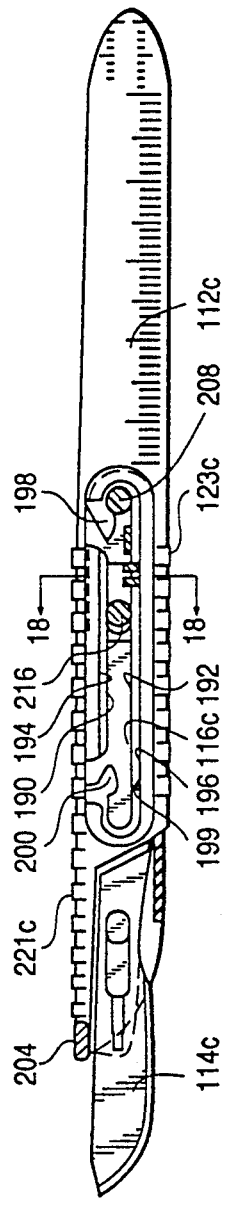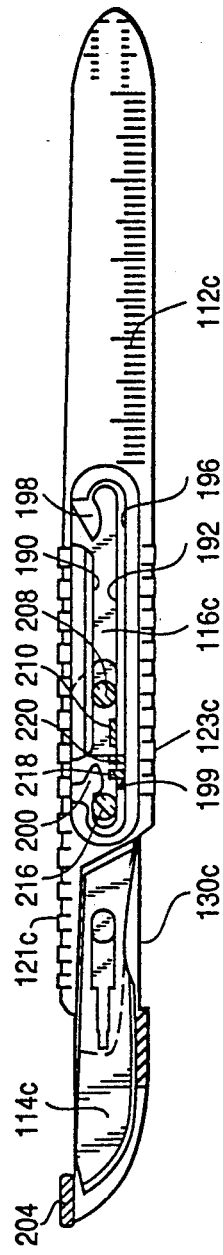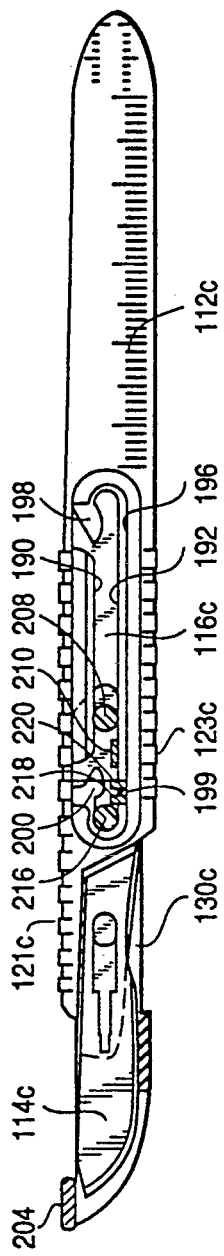

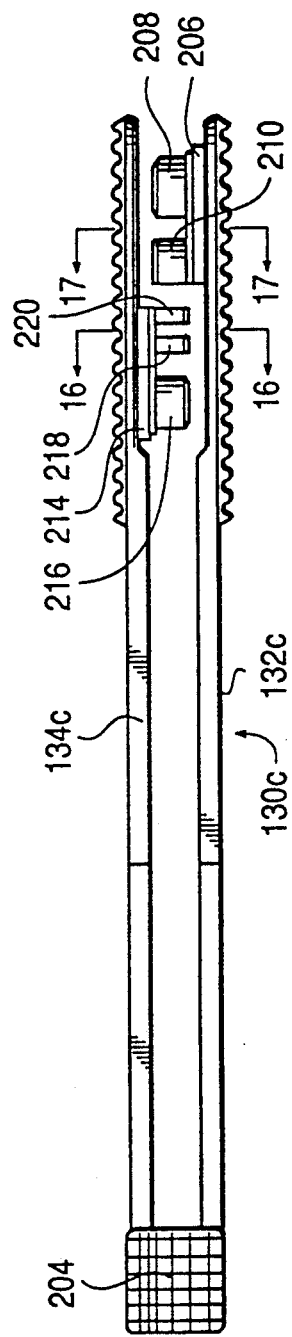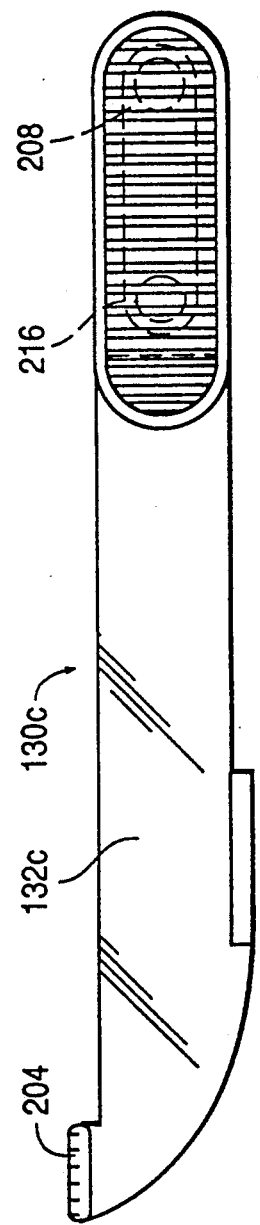

DISPOSABLE SURGICAL SCALPEL WITH SAFETY GUARD

This application is a continuation-in-part of pending application Ser. No. 07/808,891, filed Dec. 18, 1991, now allowed.

BACKGROUND OF THE INVENTION

The present invention relates to a surgical scalpel and particularly relates to a scalpel having a guard movable along the scalpel handle and blade between a protective position temporarily overlying and covering the blade and a retracted position exposing the blade for use. The invention also relates to a scalpel wherein the guard may additionally be moved into a permanent protective position permanently covering and overlying the blade.

Disposable scalpels are well known in the art and often comprise a handle, typically formed of a plastic material, to which is attached either permanently or detachably, a scalpel blade. Such disposable scalpels are conventionally packaged in sterile containers, e.g., flexible plastic packages or pouches. Once removed from the container, the blade is typically exposed for use. This, of course, also exposes the blade to all individuals, doctors, nurses, medical technicians, etc., associated with a surgical procedure, as well as those individuals charged with the disposal of the used scalpel. Thus, even with the exercise of great care, individuals are frequently inadvertently cut by the exposed blade. The dangers of being cut and transmission of infectious diseases when cut by a used blade are thus ever-present. Even when using scalpels having blades which are detached after use and disposed in a sharps container, those individuals handling the scalpels, blades or sharps containers remain at risk.

Scalpels having sheaths affording individuals protection against being cut by exposed blades are known in the prior art. For example, in U.S. Pat. No. 3,906,626, there is disclosed a sheath for a scalpel which is movable between a retracted position, exposing the blade for use, and an extended position, substantially wholly enclosing the blade.

This scalpel also provides a sheath movable into a third and permanently locked position overlying the blade, whereby the blade cannot be reused and individuals, including those charged with the disposal of the blade, are protected from being cut by the blade. This scalpel, however, has many drawbacks. The blade lacks stability in the hands of the surgeon because the sheath completely overlies the handle in the retracted position of the sheath which corresponds to the use position of the scalpel. That is, the surgeon must grasp the sheath, not the handle, in order to use the scalpel. There is accordingly a danger of play between the sheath and the handle when the scalpel is used by the surgeon. Further, two hands are necessary to displace this sheath between a position exposing the blade for use and its protective position. These and other disadvantages of the scalpel disclosed in that patent will become apparent from reference to the following description of the present invention.

SUMMARY OF THE INVENTION

According to the present invention, there is provided a novel and improved disposable scalpel or knife, comprising an elongated handle having an engaging surface located on the handle, a blade permanently secured adjacent one end of the handle and a guard movably mounted to the handle for sliding movement relative to the handle between a temporary protective position covering the blade and a retracted position exposing the blade for use. The guard is an integrally molded piece of plastic formed in a U-shaped channel which comprises a pair of side members extending downwardly from an upper surface. The side members are positioned adjacent opposite sides of the handle, wherein the resiliency of the guard forces a guide arm on each side member into engagement with the engaging surface on the handle. The resiliency of the guard prevents the side members from spreading apart and thereby prevents the removal of the guard from the handle. The guard is movable along the engaging surface in response to sliding movement of the guard relative to the handle between the protective and retracted positions. Furthermore, the scalpel comprises a locking means for releasably maintaining the guard in the temporary protective position and the retracted position.

In another embodiment of the present invention, the locking means further comprises a wedge disposed on the engaging surface and a latch disposed on the guide arm of the side members so as to allow the guard to be positioned in a permanently protective position.

To locate the guard into the protective position permanently covering the blade, the guard is moved forwardly past the temporary protective position and against the bias of the wedge located at the forward end of the engaging surface on the handle. Upon displacing the latch on the guard arm forward of the wedge, the wedge engages the latch so as to prevent rearward movement of the guard. As a result, the guard is locked in the permanent protective position.

In both of the aforementioned embodiments, the lower surface of the handle is completely exposed and the upper surface of the handle is partially exposed in all positions of the guard. Furthermore, when the guard is in the retracted position, the upper surface of the guard and the upper surface of the handle form a continuous upper surface. Moreover, the handle comprises a receiving cavity which contributes to the prevention of pivotal movement of the guard relative to the handle in the plane of the handle. As a result, when the guard is in the retracted position, the upper surface of the scalpel operates as a single non-disjoint surface. It will also be appreciated from the ensuing description and drawings that the guide arms are shaped for cooperation with the engaging surface on the handle so as to maintain the guard in positions straddling the handle in all positions of the guard along the handle. In other words, the guide arms and engaging surface also cooperate to prevent the guard from pivoting in the plane of the handle.

In another embodiment of the present invention, there is provided a scalpel comprising an elongated handle having a slot opening through and between opposite sides of the handle, a blade carried by the handle adjacent one end thereof and a guard movably mounted to the handle for sliding movement relative to the handle between a protective position covering the blade and a retracted position exposing the blade for use. The guard includes side members overlying opposite sides of the handle, respectively, and has an element connecting the side members one to the other and disposed in the slot. The element is movable along the slot in response to sliding movement of the guard relative to the handle between the protective and retracted positions. A locking member is carried by the handle in the slot for engaging the element in the protective position of the guard relative to the handle for releasably maintaining the guard in the protective position thereof and movable to enable the guard to move from the protective position toward the retracted position. Means are carried by the handle which cooperate with the element in the retracted position of the guard to releasably maintain the guard in the retracted position relative to the handle.

In another embodiment of the present invention, a single finger formed within the slot cooperates with the element to maintain the guard detented in each of its retracted and temporary positions as well as in a permanent protective position. In its temporary protective position, the finger has a cam follower surface engaging the rear edge of the element to prevent rearward sliding movement of the guard relative to the handle. A smaller finger along the opposite side of the slot adjacent its forward end engages the forward edge of the element to prevent the guard from sliding forwardly from its temporary protective position into its forwardmost permanent protective position. The guard is slidable rearwardly into its retracted position by sliding the element along the slot and biasing the first-mentioned finger outwardly. When the element engages the rear end of the slot, a second cam follower surface on the first finger engages the forward edge of the slot to detent the guard in its retracted position.

To move the guard into its permanent locking position, the guard is moved forwardly past its temporary protective position and against the bias of the small finger at the forward end of the slot into its permanent locking protective position. The first finger resiliently bears against the element during its forward sliding movement until the guard reaches its permanently locked position. At that time, the first finger is biased into the slot and into the rearward path of movement of the element, thereby locking the guard in its forwardmost permanent protective position. These locking means, including the first finger and the small forward finger, lie wholly within the confines of the slot of the handle. Thus, no lateral or transverse movement is required to move the guard or detent it in its protective or retracted positions.

In another embodiment of the present invention, a pair of forwardmost finger locks, rear finger detents and forwardly extending locking fingers are provided in the slot and, in conjunction with the previously described small forward finger, maintain the guard in the retracted, temporary protective and permanently locked positions. This form is used where large scalpel blades are necessary which require a longer slot.

In yet another embodiment of the present invention, the scalpel includes a one-piece molded guard having side members, each of which has a pin for projecting inwardly within the slot in the scalpel handle. One side member also includes adjacent its pin a pair of inwardly projecting latching detents, while the opposite side member adjacent its pin includes a single inwardly projecting latching detent. The handle slot in this embodiment has a longitudinally extending central rib defining a pair of tracks along its opposite sides. A raised catch or projection extends along one of the tracks. In this form, the pins and latching detents of the side members are inserted into the opposite sides of the handle slot with the latching detents engaging on opposite sides of the central rib and the handle. The latching detents therefore maintain the side members along opposite sides of the handle, preventing their lateral outward movement away from one another and the handle. The pins also engage between the opposite sides of the handle slot, including the central rib for guiding the guard along the handle and preventing pivotal movement of the guard relative to the handle in the plane of the handle.

In this form, the guard is similarly movable between a retracted use position for the scalpel, a temporary protective position and a permanent locked position overlying the scalpel blade. To accomplish this, inwardly depending fingers are disposed at opposite ends of the slot for engaging over the pins. Thus, in the retracted position of the guard, the pin on one of the side members is located in the end of the slot past the finger, which retains the guard in the retracted position. When the guard is moved forwardly along the slot, the forwardmost pin engages beyond the forwardmost finger and the forwardmost latching detent engages the catch along the handle track, temporarily preventing further movement of the guard in the forward direction relative to the handle. The pin of the opposite side member prevents rearward movement of the guard relative to the handle. To locate the guard in a permanent protective position relative to the scalpel blade, the guard is pushed forwardly from the temporary position into the permanent position, with the first latching detent riding over the catch whereby the catch is disposed between the pair of latching detents on the one side member, preventing movement of the guard in either longitudinal direction. Note in this embodiment that the latching detents of each side member maintain the side members closely adjacent the handle.

The scalpel of the present invention affords various additional advantages and features in comparison with conventional scalpels including those with protective sheaths. For example, an edge of the handle of the scalpel blade, as discussed previously, is fully exposed in all positions of the guard so that control of the cutting edge by the surgeon may be maintained by direct finger contact with the scalpel handle during use. Moreover, the guard is slidable along the handle between all positions using only one hand. It does not require two hands to move the guard between its protective and retracted positions. Further, the guard is slidable between retracted and temporary protective positions multiple times, whereby the scalpel may be used, set aside with the guard in its temporary protective position, and then reused with the guard movable again into its retracted position. Still further, the construction of the handle and guard may be of all plastic material whereby the scalpel may be formed and assembled inexpensively.

Accordingly, it is a primary object of the present invention to provide a novel and improved disposable scalpel with a guard movable between a retracted position exposing the scalpel blade for use, a temporary protective position overlying and covering the blade, protecting individuals from the blade, and a permanent protective position overlying and covering the blade, whereby the guard cannot be removed from its permanent protective position without effectively destroying the scalpel or the guard.

These and further objects and advantages of the present invention will become more apparent upon reference to the following specification, appended claims and drawings.

BRIEF DESCRIPTION OF THE DRAWING FIGURES

FIG. 1 is a side elevational view of a disposable scalpel with guard constructed in accordance with the present invention and illustrating the guard in a retracted position exposing the blade for use.

FIG. 2 is a side plan view of a first embodiment of the handle of the present invention, without the attaching guard.

FIG. 6 is a cross-sectional view of a first embodiment of the scalpel of the present invention taken generally on line C—C of FIG. 1, wherein the guard is in the retracted position.

FIGS. 15, 16 and 17 are respective side elevational views of a fourth embodiment of the present invention with one side member of the guard removed and illustrating the guard in a temporary protective position, a retracted position exposing the blade for use, and a permanent protective position, respectively;

FIGS. 18, 19 and 20 are views similar to FIGS. 15, 16 and 17, respectively, illustrating a fifth embodiment of a scalpel according to this invention;

FIG. 21 is a side elevational view of a sixth embodiment of the disposable scalpel of the present invention, with one side of the guard omitted, illustrating the internal connection between the other side of the guard and the scalpel handle with the guard in a retracted position;

FIG. 22 is a side elevational view similar to FIG. 21, with the guard in a temporary protective position;

FIG. 23 is a view similar to FIG. 21, with the guard illustrated in a permanent protective position;

FIG. 24 is an enlarged top plan view of a guard for use in the embodiment illustrated in FIG. 21;

FIG. 25 is a side elevational view of the guard illustrated in FIG. 24;

DETAILED DESCRIPTION OF THE DRAWING FIGURES

Reference will now be made in detail to a present preferred embodiment of the invention, an example of which is illustrated in the accompanying drawings.

Figure 7:
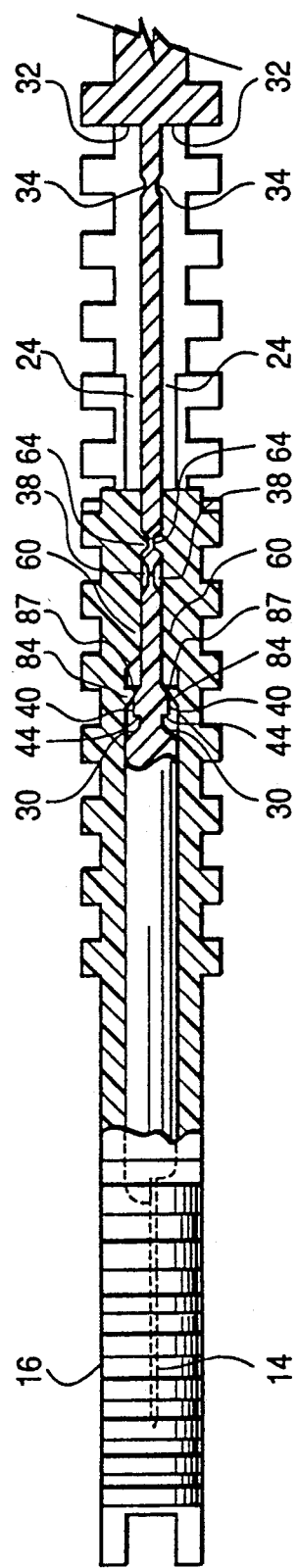
FIG. 7 is a cross-sectional view of a first embodiment of the scalpel of the present invention taken generally on line C—C of FIG. 1, wherein the guard is in the temporary protective position.
Figure 8:
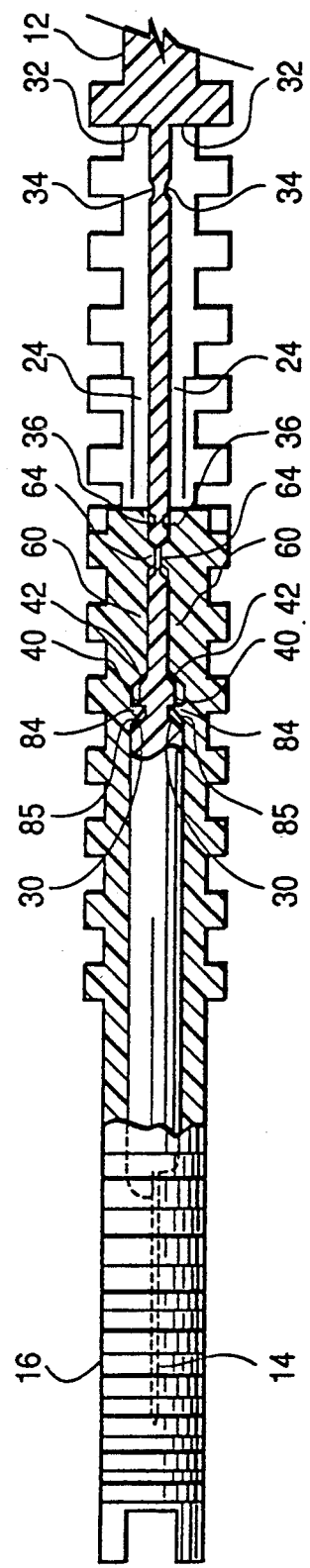
FIG. 8 is a cross-sectional view of a first embodiment of the scalpel of the present invention taken generally on line C—C of FIG. 1, wherein the guard is in the permanently protective position.

Referring now to FIG. 1, a scalpel constructed in accordance with the present invention is illustrated and generally designated 10. Scalpel 10 includes a handle 12, a blade 14 and a guard 16. Preferably, the blade 14 is permanently secured at one end of handle 12, for example, by staking. However, various sizes of blades 14 may be permanently or releasably attached to handle 12, depending on the nature of the use of the scalpel 10. The handle 12, which comprises an upper surface or edge 18 and a lower surface or edge 20, and a first side and second opposite side (not shown), preferably is formed entirely of a plastic material. The handle 12 also comprises an engaging surface 22 (shown in FIG. 2), for example, a channel, which is located proximate the blade end of the handle 12. As discussed below, the guard 16 is movably mounted within the engaging surface 22 (shown in FIG. 2) of the handle 12, such that the guard 16 is movable along the length of the engaging surface between a plurality of positions including a retracted position exposing the blade 14 for use as illustrated in FIG. 1, a temporary protective position covering and overlying the blade 14 as illustrated in FIG. 7 and a permanently locked position covering the blade 14 as illustrated in FIG. 8.

Turning to FIG. 2, a side plan view of a first embodiment of the handle 12 of the present invention is shown, without the attaching guard 16. As shown in FIG. 2, the handle 12 comprises an engaging surface 22 which is located proximate the blade end of the handle 12. The guard 16 (not shown) contacts the engaging surface 22, wherein the engaging surface 22 in conjunction with the guard 16 secures the guard 16 to the handle 12 and allows the guard 16 to move along the length of the engaging surface 22. In the embodiment of the invention shown in FIG. 2, the engaging surface 22 comprises a channel, hereinafter referred to as a keyway 22.

The keyway 22 is formed by substantially similar grooves 24 (only one is shown) on each side of the handle 12 at the same location and each groove 24 is defined by upper and lower ledges 26,28 and forward and rearward edges 30,32 which function as forward and rearward stops, respectively. Preferably, the grooves 24 begin and end at the same location on each side of the handle 12, are parallel to one another, and are located at the same vertical position on each side of the handle 12. The keyway 22 is parallel to the longitudinal axis of the handle 12. For the purpose of clarity, the keyway 22 is said to have a forward portion, which is defined as the half of the keyway 22 closest to the end of the handle 12 securing the blade 14 and a rearward portion, which is the defined as the half of the keyway 22 farthest from the blade end.

Furthermore, each groove 24 of the keyway 22 comprises a first detent 34, for example, a notch or an opening, located in the rearward portion of the keyway 22 and a second detent 36 and third detent 38 located in the forward portion of the keyway 22. The detents 34,36,38 function to releasably maintain the movable guard 16 in the various positions. The keyway 22 also comprises two latch wedges 40, each having an angled end 42 and a locking end 44. One latch wedge 40 is disposed in each groove 24 between the third detent 38 and the forward edge 30 of the groove 24. Each latch wedge 40 is formed such that the locking end 44 faces the forward edge 30 and the angled end 42 faces the rearward edge 32. Preferably, the locking end 44 of each latch wedge 40 is perpendicular to both the longitudinal and vertical axis of the keyway 22.

The handle 12 also comprises a plurality of ribs 46 longitudinally spaced one from the other along the forward portion of the upper edge 18 of the handle 12. Similar ribs 48 are disposed along the lower edge 20 and the sides of the handle 12. The ribs 46,48 facilitate gripping the scalpel 10 by the surgeon during use and are exposed in all positions of the scalpel's guard 16. Furthermore, the handle 12 forms a receiving cavity for a portion of the guard 16, wherein the receiving cavity contributes to the prevention of pivotal movement of the guard 16 relative to the handle 12.

More specifically, the width of the handle 12 surrounding the keyway 22 is reduced so as to define an upper surface 50 of the receiving cavity and a lower surface 52 of the receiving cavity, on each side of the handle 12. As discussed hereinafter, the receiving cavity formed by the handle 12 provides additional means of securing the guard 16 to the handle 12 so that the guard 16 and the handle 12 operate as an unit with the guard 16 in the retracted position. Also provided along one and preferably both side faces of the handle 12, is dimensional indicia, for example, centimeters, as shown in FIG. 2.

Figure 4:
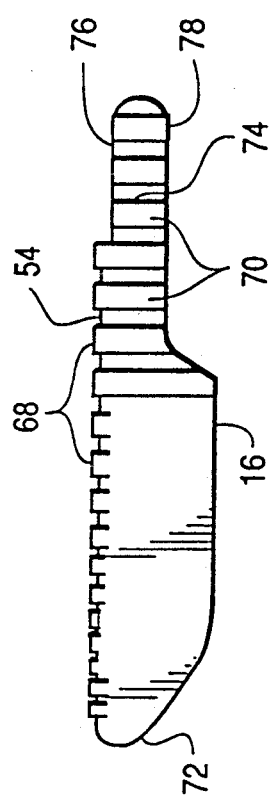
FIG. 4 is a side plan view of the guard shown in FIG. 3.
Figure 3:
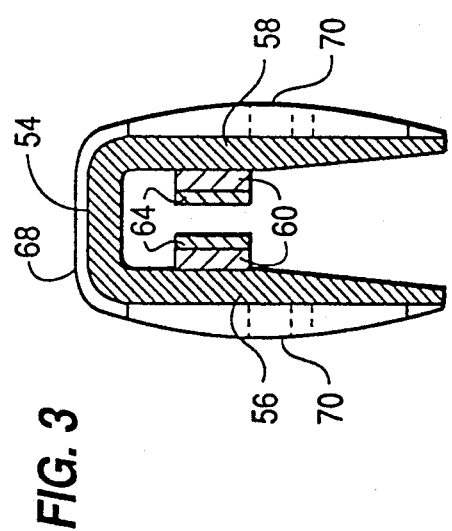
FIG. 3 is a cross-sectional view of a first embodiment of the guard of the present invention taken generally on line A—A of FIG. 1.
Figure 5:
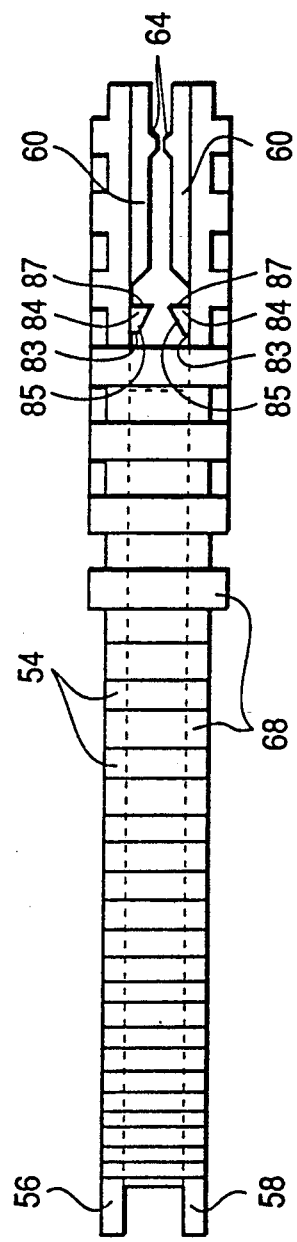
FIG. 5 is a top plan view of a first embodiment of the guard of the present invention.

FIGS. 3–5 illustrate the guard 16 of the present invention. More specifically, FIG. 3 is a cross-sectional view of a first embodiment of the guard 16 of the present invention taken on line A—A of FIG. 1. As shown in FIG. 3, the guard 16 is preferably integrally molded of one piece of plastic so as to form a U-shaped channel comprising an upper surface 54 and elongated side members 56,58 which extend downwardly from the upper surface 54. Each side member 56,58 comprises an inwardly extending flange or key 60 which functions to movably mount the guard 16 to the handle 12. Each key 60 is substantially rectangular in shape and has a height (i.e., breadth measured perpendicular to the longitudinal axis of the handle 12) such that when the key 60 is positioned in the groove 24 of the keyway 22, the key 60 engages the upper and lower ledges 26,28 of the keyway 22. Furthermore, a latching detent 64 is disposed on each key 60. The latching detents 64 engage with the detents 34,36,38 disposed in the keyway 22 so as to releasably maintain the guard 16 in various positions along the keyway 22. The two side members 56,58 preferably are mirror images of one another.

Furthermore, as illustrated best in FIG. 4, the guard 16 also comprises a plurality of ribs 68 longitudinally spaced one from the other along the upper surface 54 of the guard 16. Similar ribs 70 are disposed along the rear portion of each side member 56,58. In the preferred embodiment of the invention, as shown in FIG. 1, the ribs 46,48 on the handle 12 align vertically with the ribs 68,70 on the guard 16, when the guard 16 is in the retracted position. As previously stated, the ribs 46,48,68,70 facilitate gripping the scalpel 10 by the surgeon during use. However, the ribs 68,70 on the guard 16 also provide a frictional contact surface readily and easily gripped between an individual's fingers for sliding the guard 16 between and into its various positions along the handle 12.

As shown in FIG. 4, which is a side plan view of the guard 16 shown in FIG. 3, each side member 56,58 comprises an elongated side having a forward end 72, for example an arcuately shaped end, and a guide arm 74 formed on the rear end. Each guide arm 74 (only one is shown) is parallel to the longitudinal axis of the elongated side and is free from attachment with the top surface 54 of the guard 16. As a result, each guide arm 74 comprises an upper edge 76 and lower edge 78. Also, each guide arm 74 is formed so that the height of the guide arm 74 (i.e., breadth of the guide arm 74 measured perpendicular to the longitudinal axis of the handle 12) is such that when the guard 16 is in the retracted position, the upper edge 76 and the lower edge 78 of each guide arm 74 are sufficiently close to the upper and lower surfaces 50,52 of the receiving cavity formed by the handle 12. The receiving cavity functions to prevent pivotal movement of the guard 16 relative to the handle 12 when the guard 16 is in the retracted position.

FIG. 5 depicts a top plan view of the guard 16 of the first embodiment of the present invention. As shown in FIG. 5, the inwardly extending key 60 is formed on each side member 56,58 on the rear end of the guide arm 74 of each side member 56,58. The length of the key 60 (i.e., breadth measured parallel to the longitudinal axis of the handle 12) preferably is greater than the height of the keyway 22. It is significant that each key 60 engage the upper and lower ledges 26,28 of the keyway 22 and that each key 60 is elongated in the keyway 22 so that any torquing action on the guard 16 tending to pivot the forward end of the guard 16 away from the blade 14 is forcefully resisted by the engagement of the key 60 with the upper and lower ledges 26,28 of the keyway 22.

An inwardly extending latching detent 64 is formed on the key 60 on each guide arm 74. The latching detent 64 disposed on each key 60 engages with the detents 34,36,38 formed in the keyway 22 so as to releasably maintain the guard 16 in either the retracted position or the temporary protective position. Furthermore, each guide arm 74 comprises an inwardly extending latch 84 located forward of the key 60. Each latch 84 comprises a generally triangular ramp having an angled end 85 and a locking end 87. Preferably, similar to the latch wedges 40 disposed in the keyway 22, the locking end 87 is perpendicular to both the longitudinal and vertical axis of the keyway 22. The lower portion 83 of the angled end 85 of each latch 84 is also perpendicular to both the longitudinal and vertical axis of the keyway 22. The lower portion 83 of the angled end 85 of each latch 84 provides a positive stop when engaging the forward edge 30,32 of each groove 24 of the keyway 22. Further, the lower portion 83 is sufficiently minimal so as to not prevent the latch 84 from passing over the latch wedge 40. The function of the positive stop is to prevent outward movement of the guide arms 74 upon positioning the guard 16 in the permanently protected position. The angled end 85 of the latch 84 faces the angled end 42 of the latch wedge 40 when the guard 16 is in the retracted or temporary protective position.

To assemble the guard 16 and the handle 12 to one another, the guide arms 74 of the side members 56,58 are spread apart such that the key 60 and the latch 84 on the guide arm 74 on one side member 56, are received in the groove 24 on one side of the handle 12, while the key 60 and the latch 84 on the guide arm 74 on the other side member 58 are received in the groove 24 on the other side of the handle 12. However, because of the resiliency of the guard 16, the guide arms 74 return to their original position, wherein the keys 60 on the guide arms 74 are positioned within the keyway 22 on the respective sides of the handle 12. The engagement between the keys 60 and the grooves 24 of the keyway 22 prevent the guard 16 from separating from the handle 12. However, the keys 60 are movable along the length of the keyway 22. As a result, the guard 16 is mounted for longitudinal sliding movement relative to the handle 12. It will be appreciated that the engagement between each guide arm 74 and the handle 12 can be reversed, wherein the key 60 is mounted on the handle 12 and the keyway 22 is formed on the guide arm 74.

Referring now to the embodiment hereof illustrated in FIGS. 6-8, which are cross-sectional views of the preferred embodiment of the present invention taken along line C—C of FIG. 1, the guard 16 of the scalpel 10 is depicted in a retracted position exposing the blade 14 for use in FIG. 6, a temporary protective position covering the blade 14 in FIG. 7 and a permanently locked position covering the blade 14 in FIG. 8. Permanent locking position means a position of the guard 16 relative to the handle 12 where the guard 16 cannot be retracted or displaced from its permanent locked position without destroying either the guard 16, handle 12 or both.

Turning to FIG. 6, the guard 16 is shown fully retracted exposing the blade 14 for use. As shown in FIG. 6, in the retracted position the rear end of each side member 56,58 of the guard 16 (i.e., guide arm 74) engages the rearward edges 32 of the grooves 24 forming the keyway 22. Furthermore, the latching detents 64 on the keys 60 of the guard 16 engage with the first detent 34 formed in each groove 24. The resiliency of the guard 16 forces the engagement between the latching detents 64 on the key 60 and the first detents 34 on the keyway 22, thereby maintaining the guard 16 in the retracted position.

The resilient nature of the guide arms 74 of the guard 16 enables the guard 16 to be detented in its retracted position yet allows the sliding movement of the guard 16 to the temporary protective position shown in FIG. 7. More specifically, to move the guard 16 to the temporary protective position, the latching detents 64 on each guide arm 74 of the guard 16 are biased outwardly away from one another and are removed from the first detent 34 of the keyway 22. Each key 60 on the guard 16 travels forward in the corresponding groove 24 of the keyway 22 until the latching detents 64 disposed on each key 60 are adjacent the second detents 36 in the keyway 22, wherein the resilient nature of the guard 16 forces the latching detents 64 on each key 60 into engagement with the second detents 36 thereby securing the guard 16 in a second position. The position of the second detent 36 in each groove 24 of the keyway 22 is selected such that upon engagement with the latching detents 64 of the guard 16, the guard 16 is completely covering the blade 14, as shown in FIG. 7.

As shown in FIG. 1, it will be appreciated that by holding the handle 12 in the palm of the individuals hand and placing the thumb and index fingers on the ribs 70 disposed on the side members 56,58 of the guard 16, the guard 16 may be advanced from the retracted position to the temporary protective position and vice versa, as required. As previously stated, the latching detent 64 on the key 60 on each guide arm 74 is resiliently displaced so as to enable each key 60 to pass along the groove 24 between the various positions. It is significant that the guard 16 may be disposed in either direction with only one hand, thereby freeing the other hand for work.

After use and when it is desirable to dispose of the scalpel 10, the guard 16 may be advanced into the permanently locked position illustrated in FIG. 8. To locate the guard 16 in the permanent locked position covering the blade 14, the guard 16 is displaced forwardly from the position illustrated in FIG. 7 to the position illustrated in FIG. 8. In displacing the guard 16 forwardly, similar to moving the guard 16 from the retracted position to the temporary protective position, the latching detent 64 on each side member 56,58 of the guard 16 is biased outwardly away from one another and is removed from the second detent 36 on each groove 24 of the keyway 22. As the guard 16 is displaced forward, the angled end 85 of the latch 84 on each guide arm 74 engages the angled end 42 of the latch wedge 40 on each groove 24, and the latch 84 completely rides over the latch wedge 40 such that the locking end 44 of the latch wedge 40 and the locking end 87 of the latch 84 face one another. Specifically, upon the latch 84 engaging the latch wedge 40, the latch 84 resiliently bears against the latch wedge 40. As the latch 84 traverses the latch wedge 40, the latch 84 and consequently the guide arms 74, are displaced outwardly so as to allow the latch 84 to pass over the latch wedge 40. Upon passing over the latch wedge 40, the latch 84 is again forced by the resilient nature of the guard 16 into engagement with the keyway 22.

Figure 9:
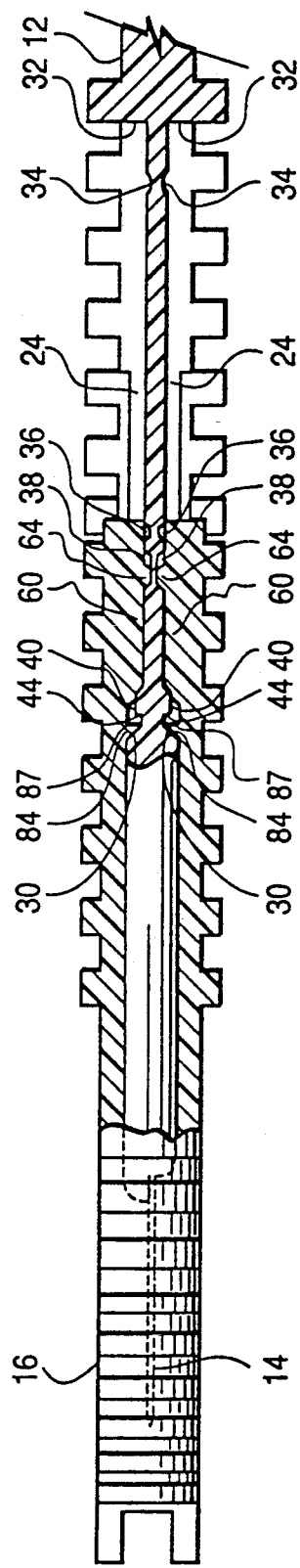
FIG. 9 is a cross-sectional view of a first embodiment of the scalpel of the present invention taken generally on line C—C of FIG. 1, wherein the guard is in the most forward position relative to the handle.

Once the latch 84 is completely forward of the latch wedge 40, the latching detent 64 on each side member 56,58 of the guard 16 engage the third detent 38 in the corresponding groove 24 of the keyway 22 so as to stabilize the guard 16 in a permanently locked position. Rearward movement of the guard 16 relative to the handle 12 is prevented in this permanently locked position by the engagement of the locking end 87 of the latch 84 against the locking end 44 of the latch wedge 40, which are preferably parallel to one another and therefore cannot be biased out of the path of one another as is shown in FIG. 8. Further forwardly movement of the guard 16 is prevented by the engagement of the latch 84 with the forward edge 30 of the grooves 24 as is shown in FIG. 9. Thus, the guard 16 is permanently secured in a position covering the blade 14.

It will be appreciated that throughout the full range of sliding movement of the guard 16 relative to the handle 12, the resiliency of the guard 16 functions to prevent the side members 56,58 of the guard 16 from spreading laterally outward away from the handle 12.

Figure 10:
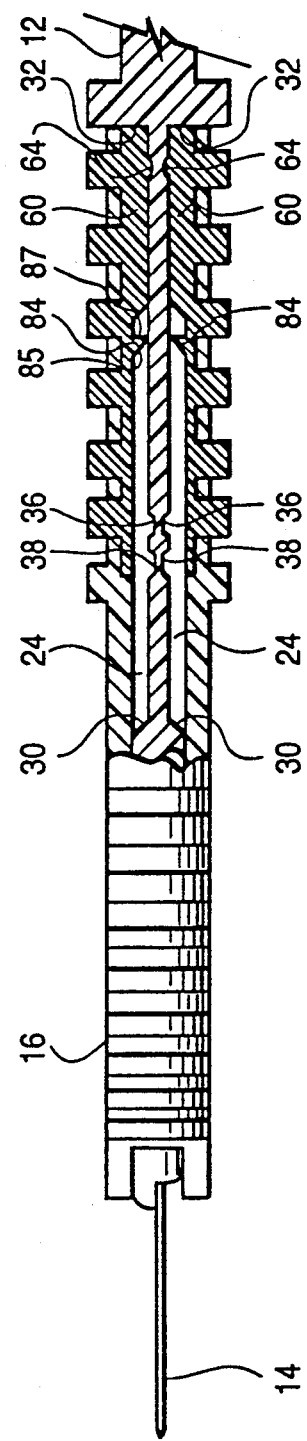
FIG. 10 is a cross-sectional view of a second embodiment of the scalpel handle of the present invention.

In a second embodiment of the present invention, as shown in FIG. 10, the latch wedge 40 disposed on the forward portion of each keyway 22 in the first embodiment, which cooperates with the latch 84 on the guide arm 74 to permanently secure the guard 16 in a position covering the blade 14, is removed from each keyway 22. As a result, the guard 16 is movably between the temporary protective position covering the blade 14 and the retracted position exposing the blade 14. However, without the latch wedge 40 in the keyway 22, the guard 16 cannot be located in the permanent protective position.

Variations of the first and second embodiments of the present invention are possible. For example, the engagement between the guide arm 74 and the handle 12 can be reversed. More specifically, the outwardly extending key 60 can be disposed on the handle 12, and the groove 24 which receives the key 60 can be formed on the guide arm 74 of the guard 16. The resiliency of the guard 16 in conjunction with the engagement between the key 60 and the groove 24 prevent the removal of the guard 16 from the handle 12 while allowing for the longitudinal movement of the guard 16 relative to the handle 12 in the same manner as the first and second embodiments.

In another variation, additional detents are disposed along the keyway 22 so that the guard 16 can be releasably maintained at various positions which correspond to various degrees of blade exposure.

In another variation, the width of a portion of the upper edge 18 of the handle 12 above the forward portion of the keyway 22 is reduced so as to minimize the distance the guide arms 74 must be separated from one another during the mounting of the guard 16 to the handle 12.

In another variation, the angled end 85 of the latch 84 on the guide arms 74 forms a right triangle with the surface of the keyway 22 and the locking end 87 of the latch 84.

In yet another variation, the latch wedge 40, which functions to permanently secure the guard 16 in the protective position, is disposed in only one of the grooves 24 of the keyway 22.

The first and second embodiments described above provide a number of significant advantages. Because the guard 16 is secured to the handle 12 by the resiliency of the guard 16 in combination with the groove 24 on the handle 12 and the key 60 on the guard 16, no additional material or parts are required to assemble the guard 16 to the handle 12.

As yet another advantage, an edge of the handle 12 of the scalpel is fully exposed in all positions of the guard 16 so that control of the cutting edge by the surgeon may be maintained by direct finger contact with the scalpel handle 12 during use. Moreover, the guard 16 is slidable along the handle 12 between all positions using only one hand. It does not require two hands to move the guard 16 between its protective and retracted positions. Further, the guard 16 is slidable between retracted and temporary protective positions multiple times, whereby the scalpel 10 may be used, set aside with the guard 16 in its temporary protective position, and then reused with the guard 16 movable again into its retracted position. Still further, the construction of the handle 12 and guard 16 may be of all plastic material whereby the scalpel 10 may be formed and assembled inexpensively.

Figure 11:
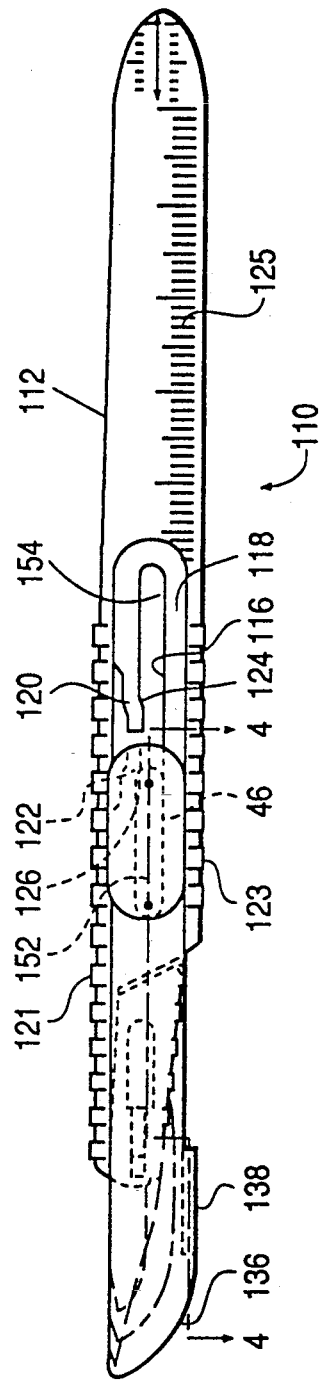
FIG. 11 is a side elevational view of a third embodiment of the disposable scalpel of the present invention and illustrating the guard in a protective position covering the blade.

Other alternate embodiments of the present invention are also possible. Referring to FIG. 11, there is illustrated a third embodiment of the scalpel of the present invention and generally designated 110. Scalpel 110 includes a handle 112 and a blade 114, preferably permanently secured at one end of handle 112, for example, by staking. It will be appreciated that various sizes of blades 114 may be permanently or releasably attached to handle 112, depending on the nature of the use of the scalpel and variously sized blades are illustrated by the dashed lines. The handle 112 is preferably formed entirely of a plastic material and, in this form, includes a central slot 116 extending through and between the opposite sides of handle 112. Slot 116 is defined by a laterally recessed rim 118 which extends about and forms the margin of slot 116, the rim 118 opening forwardly toward the blade. In this embodiment, rim 118 has a pair of longitudinally oppositely facing fingers 120 and 122 spaced inwardly from one edge of slot 116 to define cam surface followers or detents 124 and 126, respectively, facing in opposite directions. The fingers 120 and 122 terminate short of one another and are independently and resiliently movable away from their illustrated positions in slot 116.

Handle 112 also includes a plurality of ribs 121 longitudinally spaced one from the other along the upper edge of the handle and along the forward position thereof. Similar ribs 123 are disposed along the lower edge of the handle 112. The ribs 121 and 123 facilitate gripping the scalpel by the surgeon during use. As discussed hereinafter, these ribs are exposed in all positions of the scalpel's guard. Also provided along one, and preferably both side faces of the handle, is dimensional indicia, indicated 125, in this case given in centimeters.

Figure 13:
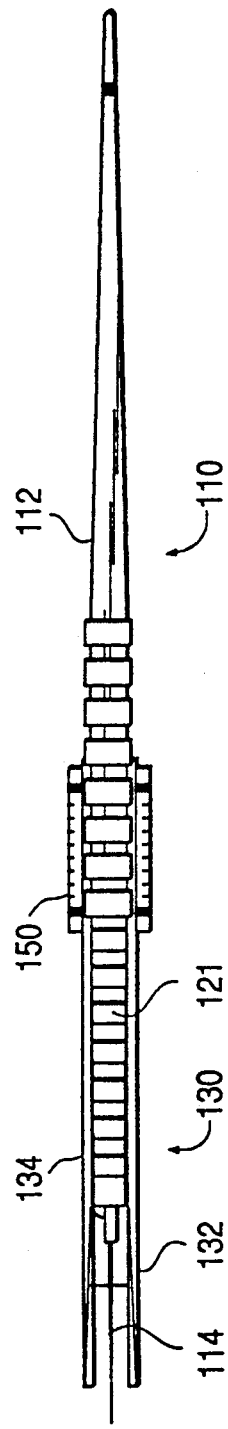
FIG. 13 is a top plan view of the scalpel illustrated in FIG. 11.
Figure 14:
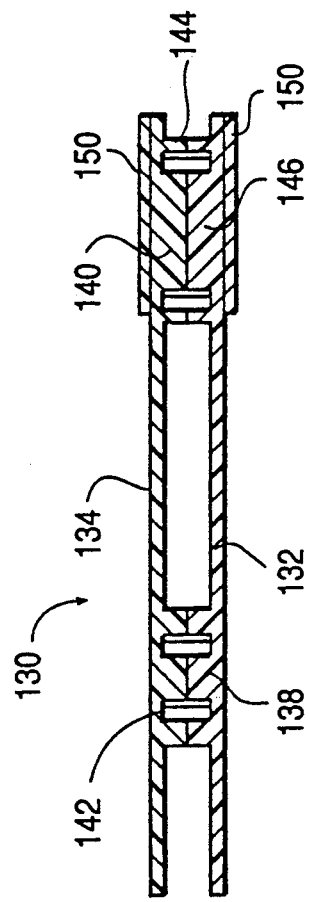
FIG. 14 is a cross-sectional view of the guard for the scalpel of FIG. 11.
Figure 26:
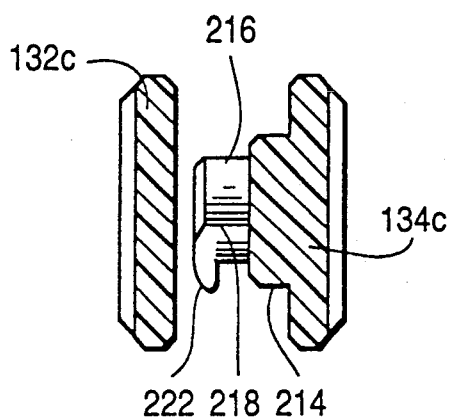
FIG. 26 is a cross-sectional view of the guard illustrated in FIG. 24 and taken about on line 16—16 in FIG. 24.

Referring now particularly to FIGS. 13 and 14, scalpel 110 includes a guard, generally designated 130, comprising a pair of elongated side members 132 and 134. Side members 132 and 134 are mirror-images of one another. Each side member includes an elongated side having an arcuately shaped forward end edge 136 and an inwardly extending flange 138 along the lower side of guard 130 adjacent its forward end. Each side member also includes an inwardly extending flange 140 substantially medially between the upper and lower edges of the guard and adjacent its rear end portion. Flanges 138 and 140 of each side member are connected to the corresponding flanges 138 and 140 of the opposite side member by pins 142 and 144, respectively, as illustrated in FIG. 14.

Figure 12:
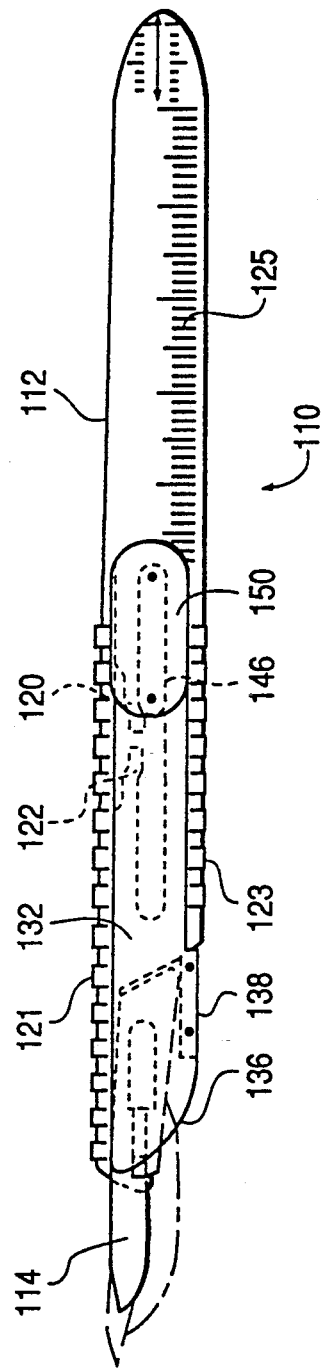
FIG. 12 is a view similar to FIG. 11 illustrating the guard in a retracted position exposing the blade for use.

The connected flanges 140 form an element 146 elongated in the longitudinal direction of the handle. Element 146 is disposed in slot 116 in the handle. The connected flanges 138 adjacent the forward end of guard 130 underlie, respectively, the edge of the blade in the protective position of the guard and the lower edge of the handle in the retracted position of the guard. For reasons discussed hereinafter, the upper edge of the side members 132 and 134 of the guard are unconnected. In its assembly with the handle, the upper and lower edges of the handle including ribs 121 and 123, respectively, thus extend through the guard, as illustrated in FIGS. 11 and 12. Guard 130 also includes a pair of side grips 150 formed along the rear end portion of the guard. The outer faces of grips 150 may be serrated or otherwise formed to provide a frictional contact surface readily and easily gripped between an individual's fingers for sliding guard 130 between and into its various positions along handle 112. Rear portions of side members 132 and 134 extend along the opposite sides of the handle within rim 118. It is significant that the side members 132 and 134 engage rim 118 and that element 146 is elongated in the slot 116 such that any torquing action on the guard tending to pivot the forward end of the guard away from the blade is forcefully resisted by the engagement of the side members against rim 118 and by the cooperation of elongated element 146 lying in a corresponding elongated portion of slot 116.

With the guard assembled to the handle as described, the guard is movable between a temporary protective position covering and overlying the blade 114 as illustrated in FIG. 11 and a retracted position exposing the blade for use, as illustrated in FIG. 12, it being appreciated that the guard is detented in both positions for temporarily fixing the guard in the selected position. As illustrated in FIG. 11, slot 116 has a forward slot portion 152 defined by the forward end of slot 116 and the inside edge of finger 122 which defines cam follower 126. Thus, cam follower 126 engages the rear trailing edge of element 146 when the guard lies in its protective position forwardmost in slot 116, as illustrated in FIG. 11. The resilient nature of finger 122 enables the guard to be detented in its protective position yet enables the guard for sliding movement from the protective position to the retracted position illustrated in FIG. 12. Thus, when an individual grasps the scalpel handle in the palm of his hand and places his thumb and index finger on the grips 150, the guard may be displaced rearwardly from its protective position against the bias of finger 122 and into the retracted position illustrated in FIG. 12. The rear finger 120 is cammed out of the way by element 146 as element 146 passes rearwardly along slot 116 such that element 146 may be disposed in the rear slot portion 154. In that position, finger 120 spring returns to the illustrated position to engage cam follower surface 124 against the leading edge of element 146, detenting the guard in the retracted position.

Similarly, by holding the handle in the palm of the individual's hand and placing the thumb and index fingers along grips 150, guard 130 may be advanced from the retracted position of FIG. 12 into the protective position illustrated in FIG. 11. In transitioning between the two positions, it will be appreciated that fingers 120 and 122 are resiliently displaced out of the way to enable the element 146 to pass along slot 116 between those positions. It is significant that the guard may be disposed in either position with only one hand, thus freeing the other hand for other work. Also, note that ribs 121 and 123 along upper and lower edges of the handle 112 are at all times exposed for gripping by the surgeon in both retracted and protective positions of the guard.

FIGS. 15–17 illustrate a fourth embodiment of the present invention wherein like reference numerals refer to like parts, followed by the letter suffix "a", there is provided a scalpel 110a having a handle 112a, a blade 114a permanently or releasably attached to the handle 112a, and a guard 130a. In this form, however, the guard is movable between a temporary protective position covering the blade illustrated in FIG. 15, a retracted position exposing the blade for use illustrated in FIG. 16, and a permanently locked position covering the blade illustrated in FIG. 17. By permanent locking position is meant a position of the guard relative to the handle where the guard cannot be retracted or displaced from its permanent locked position without destroying either the guard, handle, or both.

In this form, slot 116a includes a laterally recessed rib 118a, the rib 118a forming within slot 116a a single finger 160. As illustrated in FIG. 15, finger 160 projects forwardly and is spaced from the corresponding upper edge of slot 116a. Finger 160 includes a pair of arcuate cam follower surfaces 162 and 164 along its underside but spaced longitudinally one from the other. Finger 160 also includes a tip 166. The lower portion of finger 160 between surfaces 162 and 164 thus projects into slot 116a as illustrated in FIG. 15. Finger 160, however, is biased for movement into the path of movement of element 146a, as illustrated in FIG. 17 and is resiliently movable out of the way as discussed hereinafter. Additionally, at the forward end of slot 116a, there is provided along its lower side an upwardly projecting finger 168 spaced from the forward end wall of slot 116a.

In using this embodiment of the scalpel, the scalpel 110a would typically be provided in a sterile package with the guard 130a in the temporary protective position illustrated in FIG. 15. In that position, element 146a is disposed in a forward portion of slot 116a, bounded at its forward edge by its engagement with finger 168, which prevents further forward movement of the guard relative to the handle, and at its rear edge by engagement with the arcuate surface 162 of finger 160. The engagement between the arcuate surface 162 and the trailing edge of element 146a in the temporary protective position of the guard 130a relative to handle 112a prevents finger 160 from assuming its normal position in slot 116a, as illustrated in FIG. 17. To displace guard 130a rearwardly from the temporary protective position of FIG. 15 to its retracted position, exposing the blade 114a for use illustrated in FIG. 16, handle 112a is disposed in the user's hand and grips 150a are grasped between the thumb and index finger, whereby the guard may be moved rearwardly. Upon moving the guard rearwardly, element 146a cams finger 160 upwardly out of the way of element 146a, enabling the guard to slide rearwardly into abutment against the rear end of slot 116a. In that position, as illustrated in FIG. 16, finger 160 resiliently moves toward its normal position illustrated in FIG. 17 to engage cam follower 164 against the edge of element 146a, thereby detenting guard 130a in the retracted position.

To displace guard 130a back into its temporary protective position, the user grasps grips 150a and slides guard 130a forwardly against the bias of finger 160. Finger 160 is thus displaced out of the path of travel of element 146a until the guard is advanced sufficiently such that the leading edge of element 146a engages finger 168. At that time, finger 160 springs back such that cam follower 162 engages the trailing edge of element 146a whereby the guard is detented between fingers 160 and 168 and maintained in the temporary protective position illustrated in FIG. 15.

After use and when it is desirable to dispose of the scalpel, the guard may be advanced into its permanently locked position illustrated in FIG. 17. To accomplish this, the handle is once again disposed in the user's hand and the grip grasped between the thumb and forefinger to advance the guard forwardly. By advancing the guard forwardly, the element 146a displaces finger 168 out of the way until the leading edge of element 146a engages the forward end of slot 116a. At that time, the trailing edge of element 146a is located forwardly of finger 160, enabling finger 160 to spring into its normal position illustrated in FIG. 17, engaging the trailing edge of element 146a and blocking rearward return movement of guard 130a from its permanent protective position. Consequently, the guard is permanently locked, covering the blade, whereby individuals are protected from inadvertent, casual and non-intentional contact with the blade. The scalpel may then be handled for further disposal without the danger attendant to an exposed blade.

In another variation, referring to a fifth embodiment illustrated in FIGS. 18–20 (like reference numerals are applied to like parts as in the prior embodiments, followed by the suffix "b"), the scalpel carries substantially larger blades than disclosed in the prior embodiments and, accordingly, the range of travel of the guard relative to the handle and blade is increased. To accommodate that increase in range of travel, slot 116b is provided with a pair of forwardly extending fingers 170 and 172, respectively. Finger 170 is located adjacent the rear portion of slot 116b and has an arcuate cam follower surface 174 for engaging the leading edge of element 146b when the guard is moved to its retracted position, as illustrated in FIG. 19. Finger 172 is formed to normally project into slot 116b, as illustrated in FIG. 20, and includes an arcuate cam follower surface 176 along the underside of its forward edge. Finger 172 also includes a tip 178. Additionally, slot 116b includes at its forward end a finger 180 which projects upwardly into slot 116b, defining the forwardmost positio of the element 146b when disposed in the temporary protective position.

In using this form of the invention, scalpel 110b would typically be provided in a sterile package with guard 130b covering blade 114b in its temporary protective position. Thus, element 146b is detented between the upwardly projecting finger 180 and the cam follower 176 of finger 172. Note that the engagement of cam follower 176 and element 146b prevents finger 172 from moving into its normal position within slot 116b as illustrated in FIGS. 19 and 20. To use scalpel 110b, grips 150b are grasped between the thumb and forefinger and the guard retracted along slot 116b. This retracting movement cams finger 172 out of the way of movement of element 146b and also cams finger 170 outwardly such that element 146b may be disposed in its rearmost position with its trailing edge against the rear end of slot 116b. In that position, the forward edge of the element 146b is engaged by the arcuate cam follower surface 174 of finger 170 whereby element 146b and hence guard 130b is detented in the retracted position.

After use, guard 130b may be displaced forwardly into its temporary protective position illustrated in FIG. 18. In displacing guard 130b forwardly, fingers 170 and 172 are displaced upwardly out of the way of movement of element 146b until the leading edge of element 146b engages finger 180. In that position, it will be appreciated from a review of FIG. 18 that the element 146b and hence guard 130b is detented between finger 180 and the arcuate cam follower surface 176 of finger 172 whereby the guard 130b is releasably maintained in the temporary protective position. It will be appreciated that the guard may be displaced rearwardly and forwardly multiple times between the retracted and temporary protective positions.

When the scalpel is to be discarded, the guard is advanced into its forwardmost position, displacing finger 180 downwardly out of the way of its movement. When the leading edge of element 146b engages the forward wall of slot 116b, the trailing edge of element 146b clears finger 172 to enable it to return to its normal position illustrated in FIG. 20 to locate tip 178 in engagement against the trailing edge. Finger 172 cannot be cammed out of the way and thus prevents rearward movement of guard 130b to permanently lock guard 130b in its permanent protective position.

In yet another variation, referring now to a sixth embodiment illustrated in FIGS. 21-28, there is disclosed a scalpel wherein like reference numerals are applied to like parts as in the previous embodiments, followed by the suffix c. Thus, in FIGS. 21-23, there is illustrated a handle 112c having a blade 114c secured to the end of handle 112c and including a central slot 116c. In this form, slot 116c includes centrally disposed upper and lower ribs 190 and 192, respectively (see FIG. 28), defining tracks 194 and 196 along opposite sides thereof, respectively. A catch 199 comprised of a generally triangular ramp is disposed in the slot 116c along track 196 in a forward portion of slot 116c. Adjacent the opposite ends of slot 116c, there are provided fingers 198 and 200, respectively, which project into the slot and face in opposite directions. Fingers 198 and 200 are independently and resiliently movable away from their illustrated positions in slot 116c. The handle 112c includes the ribs 121c and 123c along the upper and lower edges of handle 112c, similarly as in the previous embodiments for purposes of gripping the scalpel, and also the rim 118c for engaging the margins of the side members 132c and 134c of the guard which will now be described.

Figure 27:
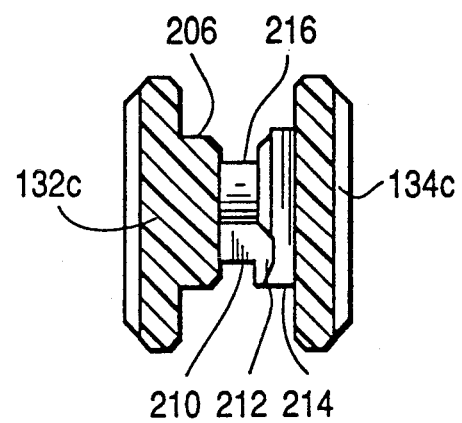
FIG. 27 is a cross-sectional view of the guard illustrated in FIG. 24 and taken generally about on line 17—17 in FIG. 24.
Figure 28:
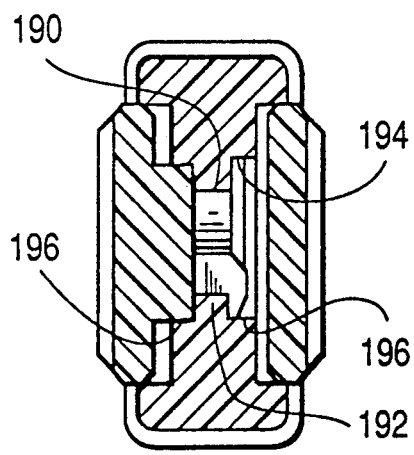
FIG. 28 is a cross-sectional view of the guard of the embodiment illustrated in FIGS. 21-27 taken generally about on line 18—18 in FIG. 21.

Referring particularly to FIGS. 24-27, the guard 130c is preferably integrally molded of one-piece and includes a pair of elongated side members 132c and 134c. The side members are secured along their forward ends and forward edges one to the other by a crosspiece 204 and are otherwise free of connection from one another. Adjacent the distal end of side member 132c is an inwardly extending boss 206 mounting an inwardly projecting cylindrical pin 208 and a latching detent 210 forwardly of pin 208. As best illustrated in FIG. 27, latching detent 210 has a downwardly turned tip 212. Side member 134c has a similar boss 214 located forwardly of boss 206. An inwardly extending cylindrical pin 216 and a pair of latching detents 218 and 220 project inwardly from boss 214. Latching detents 218 and 220 have downwardly formed tips, e.g., the tip 222 on latching detent 218, illustrated in FIG. 26.

To assemble the guard 130c and handle 112c one to the other, the side members 132c and 134c are spread apart at their distal ends such that the pin 208 and latching detent 220 are received in the slot 116c from one side of the handle, while the pin 216 and latching detents 218 and 220 are received in the slot from the opposite side of handles 116c. Because of the flexible nature of the latching detents, the tips of the detents snap past the lower rib 192 to engage on respective opposite sides thereof. Thus, the tip 212 of latching detent 210 maintains the distal end of side member 132c in close adjacency to the side of handle 112c, while the engagement of the tips of latching detents 218 and 220 along the opposite side of the central rib maintain the distal end of side member 134c adjacent the opposite side of handle 112c. Thus, the side members 132c and 134c are not directly connected to one another through slot 116c. Pins 208 and 216 bear along the upper and lower ribs 190 and 192, respectively. Consequently, the guard 130c is mounted for longitudinal sliding movement relative to the handle by the engagement of the edges of the guard side members with the rim 118c of the handle and the engagement of pins 208 and 216 in slot 116c, the tips of the latching detents maintaining the side members of the guard in close adjacency to the opposite sides of the handle, respectively.

With the guard assembled to the handle as described above, the guard is movable between a retracted position exposing the blade 114c for use as illustrated in FIG. 21, a temporary protective position covering and overlying the blade 114c as illustrated in FIG. 22, and a permanent protective position overlying blade 114c as illustrated in FIG. 23. Thus, the guard may be retracted or displaced rearwardly along handle 112c such that the pin 208 is first biased out of the rearward path of movement of the pin and then returns to its predetermined position illustrated in FIG. 21, temporarily locking the pin 208 in the rearward end of slot 116c. In this position, the guard is retracted, exposing the blade for use. To temporarily cover the blade, as illustrated in FIG. 22, the guard is displaced forwardly relative to handle 112c, with the pins and latching detents sliding along the slot 116c. Pin 216 thus engages finger 200, moves it out of the way of further forward movement of pin 216 until it resiliently flexes back into the position illustrated in FIG. 22 to releasably prevent rearward movement of the guard relative to the handle. Simultaneously, the tip 222 of the first latching detent 218 engages the initial portions of the ramp of the triangularly-shaped catch 199 along track 196 to prevent the guard from moving further forwardly in slot 116c. Thus, the guard is temporarily locked in a protective position with its forward portion overlying blade 114c. Note also that the pins 208 and 216, not only serve as guides in slot 116c, but also constitute locking means for releasably retaining the guard in the temporary protective and retracted positions in cooperation with the two locking fingers 198 and 200, respectively. Locking finger member 200 in cooperation with pin 216 releasably locks the guard in the protective position and locking finger 198 in cooperation with pin 208 releasably maintains the guard in the retracted position.

To locate the guard in a permanent locking position permanently covering blade 114c, the guard is displaced forwardly from the position illustrated in FIG. 22 to the position illustrated in FIG. 23. In displacing the guard forwardly, tip 222 rides over the ramp of catch 199 such that the tips of the latching members 218 and 220 straddle or lie on opposite sides of the catch 199. Simultaneously, the pin 216 engages in the forward end of the slot. Thus, further movement of the guard forwardly is prevented by the engagement of the pin in the forward end of the slot and the engagement of the trailing tip of latching detent 220 along the ramp of catch 199. Rearward movement of guard 130c relative to handle 112c is prevented in this permanently locked position by the engagement of the tip 222 of the forward latching detent 218 against the flat or perpendicular side of catch 199. It will be appreciated that throughout the full range of sliding movement of the guard relative to the handle, the tips of the latching detents 210, 218 and 220 prevent the side members from spreading laterally outwardly from the handle.

The embodiments described above provide a number of significant advantages. For example, an edge of the handle of the scalpel blade, as discussed previously, is fully exposed in all positions of the guard so that control of the cutting edge by the surgeon may be maintained by direct finger contact with the scalpel handle during use. Moreover, the guard is slidable along the handle between all positions using only one hand. It does not require two hands to move the guard between its protective and retracted positions. Further, the guard is slidable between retracted ad temporary protective positions multiple times, whereby the scalpel may be used, set aside with the guard in its temporary protective position, and then reused with the guard movable again into its retracted position. Still further, the construction of the handle and guard may be of all plastic material whereby the scalpel may be formed and assembled inexpensively. In the first embodiment, the guard is a one-piece molded construction, while in the other embodiments the guard may be of a two-piece molded construction.

In another advantage, in all of the embodiments hereof, it will be appreciated that the connection between the guard and handle provides a scalpel assembly of greater integrity and strength, i.e., stiffer, than either of the handle or guard individually.

As yet another advantage, the guard may be formed of a transparent or semi-transparent material. Thus, with appropriate identification markings on the blade, the type of blade can be identified by the user with the guard i its protective position overlying the blade and without the need to retract the guard. Alternatively, the guard may be opaque and have a window with or without a magnifying glass and through which window the type of blade may be identified. Various types of coated blades or edges, e.g., blades or edges coated with polymer materials, such as polytetrafluoroethylene, may be used and the invention hereof is not limited to any particular blade, coated or uncoated.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A scalpel comprising:
   an elongated handle comprising an upper and lower surface, a first and second side opposite one another, and a keyway formed by grooves positioned at the same location on said first and second side, wherein at lest one of said upper and lower surface is exposed so as to facilitate gripping the handle during use;
   a blade carried by said handle proximate to one end thereof;
   a guard movably mounted to said handle for sliding movement relative to said handle between a protective position covering said blade and a retracted position exposing said blade for use;
   said guard comprising resilient side members located proximate to said first and second side of said handle, each side member comprising a guide arm having an inwardly extending key positioned within the adjacent groove of said keyway so as to secure said guard to said handle, and
   locking means for releasably securing said guard to said handle in the retracted position and in the protective position, said locking means is movable to enable said guard to move between said protective position and said retracted position,
   whereby the resilient force of the side members maintains said key on each guide arm within the adjacent groove of said keyway so as to prevent the separation of said guard from said handle, and effects the engagement of said locking means so as to releasably secure said guard in said positions.

2. A scalpel according to claim 1 wherein said locking means comprises a plurality of detents disposed in said keyway of said handle, wherein said detents are engageable with said guide arm of said guard for releasably securing said guard in said retracted position and said protective position.

3. A scalpel according to claim 2 wherein said key on each guide arm is movable along the longitudinal axis of said keyway.

4. A scalpel according to claim 3 wherein said locking means further comprises an inwardly extending latching detent formed on said key, said latching detent engageable with said detents disposed in said keyway so as to secure said guard in said protective or retracted position, wherein said latching detent is displaced in response to sliding movement of said guard between the protective and retracted positions.

5. A scalpel according to claim 4 wherein said locking means further comprises a latch wedge disposed in said keyway and a latch disposed on said key, said latch wedge engageable with said latch upon movement of said latch forwardly of said latch wedge such that said guard is in a permanently locked position covering the blade.

6. A scalpel according to claim 1 wherein said guard is integrally molded of one piece of plastic so as to form a U-shaped channel, wherein said side members extend downwardly from an upper surface.

7. A scalpel according to claim 1 wherein said guard further comprises a plurality of ribs longitudinally spaced one from the other disposed along said upper surface and said side members so as to facilitate gripping the handle during use.

8. A scalpel according to claim 1 wherein said keyway on said handle is located on said handle such that a sufficient portion of the handle remains substantially completely exposed with the guard in the retracted position so as to allow the operator to secure the handle in one hand while shifting the position of the guard with fingers of the same hand.

9. A scalpel according to claim 1 wherein said handle further comprises a receiving cavity which engages a portion of said guard in the retracted position such that guard and handle function as an integrated unit with guard in the retracted position.

10. A scalpel comprising:
an elongated handle comprising an upper and lower surface, a first and second side opposite one another, and a keyway formed by grooves positioned at the same location on said first and second side, wherein at least one of said upper and lower surfaces is exposed so as to facilitate gripping the handle during use;
a blade carried by said handle proximate to one end thereof;
a guard movably mounted to said handle for sliding movement relative to said handle between a retracted position exposing said blade for use, a temporary protective position covering said blade, and a permanently locked position covering the blade;
said guard comprising resilient side members located proximate to said first and second side of said handle, each side member comprising a guide arm having an inwardly extending key positioned within the adjacent groove of said keyway so as to secure said guard to said handle; and
locking means for releasably securing said guard to said handle in the retracted position and in the protective position and for permanently securing the guard in the permanently locked position, said locking means is movable to enable said guard to move between said protective position and said retracted position,
whereby the resilient force of the side members maintains said key on each guide arm within the adjacent groove of said keyway so as to prevent the separation of said guard from said handle, and effects the engagement of said locking means so as to secure said guard in said positions.

11. A scalpel according to claim 10 wherein said locking means comprises a plurality of detents disposed in said keyway of said handle, wherein said detents are engageable with said guide arm of said guard for releasably securing said guard in said retracted position and said protective position.

12. A scalpel according to claim 11 wherein said key on each guide arm is movable along the longitudinal axis of said keyway.

13. A scalpel according to claim 12 wherein said locking means further comprises an inwardly extending latching detent formed on said key, said latching detent engageable with said detents disposed in said keyway so as to secure said guard in said protective or retracted position, wherein said latching detent is displaced in response to sliding movement of said guard between the protective and retracted positions.

14. A scalpel according to claim 13 wherein said locking means further comprise a latch wedge disposed in said keyway and a latch disposed on said key, said latch wedge engageable with said latch upon movement of said latch forwardly of said latch wedge such that said guard is in said permanently locked position covering the blade.

15. A scalpel according to claim 10 wherein said guard is integrally molded of one piece of plastic so as to form a U-shaped channel, wherein said side members extend downwardly from an upper surface.

16. A scalpel according to claim 10 wherein said guard further comprises a plurality of ribs longitudinally spaced one from the other disposed along said upper surface and said side members so as to facilitate gripping the handle during use.

17. A scalpel according to claim 10 wherein said keyway on said handle is located on said handle such that a sufficient portion of the handle remains substantially completely exposed with the guard in the retracted position so as to allow the operator to secure the handle in one hand while shifting the position of the guard with fingers of the same hand.

18. A scalpel according to claim 10 wherein said handle further comprises a receiving cavity which engages a portion of said guard in the retracted position such that guard and handle function as an integrated unit with guard in the retracted position.

* * * * *